United States Patent [19]

Kojima et al.

[11] Patent Number: 5,453,529

[45] Date of Patent: Sep. 26, 1995

[54] NITROIMINO COMPOUND AS INTERMEDIATE FOR INSECTICIDES AND PHARMACEUTICALS

[75] Inventors: Shigeru Kojima; Makoto Funabora; Noriaki Kawahara; Yoshiyuki Iiyoshi, all of Nakakubiki, Japan

[73] Assignee: Nippon Soda Co., Ltd., Tokyo, Japan

[21] Appl. No.: 156,485

[22] Filed: Nov. 23, 1993

Related U.S. Application Data

[63] Continuation-in-part of Ser. No. 855,681, May 5, 1992, abandoned.

[51] Int. Cl.[6] .................. C07C 309/51; C07C 249/00; C07C 249/02
[52] U.S. Cl. ............ 558/2; 540/553; 544/332; 544/330; 546/278; 548/329.1
[58] Field of Search .................. 558/2; 544/332; 540/553

[56] References Cited

U.S. PATENT DOCUMENTS 2,418,959  4/1947  Thurston et al. .................. 558/2
3,299,129  1/1967  D'Amico .................. 558/2
3,322,788  5/1967  Gompper et al. .................. 558/2 X
3,401,201  9/1968  Walton .................. 558/2 X
3,652,736  3/1972  Gutman .................. 558/2
4,880,933  11/1989  Shiokawa et al. .................. 544/332

FOREIGN PATENT DOCUMENTS 0060049  9/1982  European Pat. Off. .................. 558/2
0154975  5/1982  Germany .................. 558/2
0551393  7/1974  Switzerland .................. 558/2

*Primary Examiner*—Floyd D. Higel
*Attorney, Agent, or Firm*—Joseph C. Mason, Jr.; George B. Oujevolk; Louise A. Foutch

[57] ABSTRACT

Nitroinimo compound as intermediate for insecticides and pharmaceuticals of the formula I

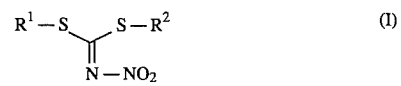

wherein $R^1$ and $R^2$ are the same or different from each other and denote lower alkyl of 1 to 4 carbon atoms.

4 Claims, No Drawings

NITROIMINO COMPOUND AS INTERMEDIATE FOR INSECTICIDES AND PHARMACEUTICALS

CROSS REFERENCE RELATED APPLICATIONS

This application is a continuation-in-part of our co-pending application entitled "Method For Preparing Heterocyclic Compounds" filed on May 5, 1992, bearing Ser. No. 07/855,681 now abandoned.

FIELD OF INVENTION

This invention relates to a novel nitroimino compound of the formula

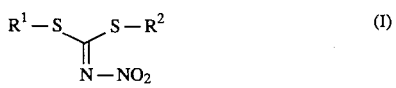

wherein $R^1$ and $R^2$ are the same or different and are lower alkyl of from 1 to 4 carbon atoms, which are useful as intermediates for insecticides and pharmaceuticals.

DESCRIPTION OF RELATED ART

The art has known that certain nitro- and cyanoimino compounds can be used as intermediates for insecticides and certain medicinal applications. Illustrative of this art is U.S. Pat. No. 4,880,933 to Shiokawa et al. An object of this invention is to provide a novel nitroimino compound which can be effectively used to manufacture insecticides such as nitrogen containing heterocyclic compounds.

SUMMARY OF THE INVENTION

This invention is a nitroimino compound of the following formula (I)

wherein $R^1$ and $R^2$ are the same or different and are lower alkyl of from 1 to 4 carbon atoms, and to a nitrogen containing heterocyclic compound of the following formula (III)

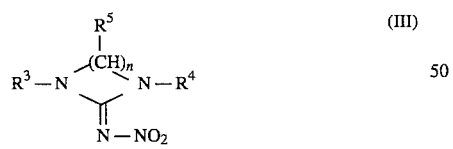

using the compound (I) as a starting material.

It was also discovered that compound (I), $(RS)_2$—C=N—$NO_2$, can be easily obtained by nitration of the corresponding $(RS)_2$—C=N—NH compound.

The process of the present invention prepares the nitrogen containing heterocyclic compound of formula (III)

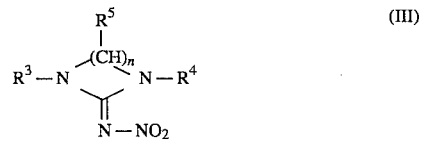

by reacting, for instance, an ester of N-nitroimidodithiocarbonic acid (formula (I)) with a diamine of formula (II): $R^3NH$—$(R^5CH)_N$—$NHR^4$, wherein $R^3$ and $R^4$ are the same or different and represent hydrogen or a lower alkyl of 1 to 4 carbon atoms optionally substituted by a heterocyclic ring comprising a five or six member ring wherein one of the ring atoms is nitrogen; such ring being optionally substituted by halogen or lower alkyl, $R^5$ is hydrogen or lower alkyl of from to 4 carbon atoms, and n is 2, 3 or 4. Preferably, the reaction takes place in a solvent medium.

Broadly, the present invention is a method for preparing a nitrogen containing heterocyclic compound which comprises:

(a) reacting a compound of formula (I)

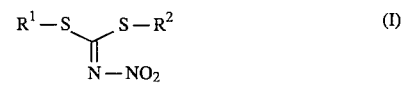

where $R^1$ and $R^2$ are the same or different, and are lower alkyl of 1 to 4 carbon atoms;

(b) with a compound of formula (II)

wherein $R^3$ and $R^4$ are the same or different and represent hydrogen, or a lower alkyl of 1 to 4 carbon atoms optionally substituted by a heterocyclic ring comprising a five or six membered ring wherein one of the ring atoms is nitrogen, such ring being optionally substituted by halogen or lower alkyl, $R^5$ is hydrogen or lower alkyl of from 1 to 4 carbon atoms, and n is 2, 3 or 4;

(c) under reaction conditions sufficient to produce a nitrogen containing heterocyclic compound of formula (III)

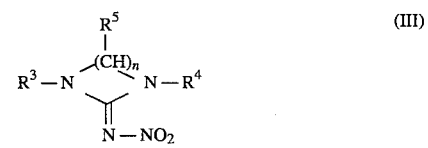

wherein $R^3$ and $R^4$ are the same or different and represent hydrogen or a lower alkyl of 1 to 4 carbon atoms optionally substituted by a heterocyclic ring comprising a five or six member ring wherein one of the ring atoms is nitrogen, such ring being optionally substituted by halogen or lower alkyl of from 1 to 4 carbon atoms, and n is 2, 3 or 4.

Preferably, the lower alkyl may be straight or branched chain of 1 to 4 carbon atoms such as methyl, ethyl, isopropyl and tertiary butyl. The halogen may be chlorine or bromine.

Examples of formula (I) compounds, where $R^1$ and $R^2$ are the same alkyl, include S,S'-dimethyl N-nitroimidodithiocarbonate and where $R^1$ and $R^2$ are different alkyl, include S-isopropyl S'-methyl N-nitroimidodithiocarbonate and S-methyl S'-t-butyl N-nitroimidodithiocarbonate.

The formula (II) compound can be prepared according to the method described in SKIN JIKKEN KAGAKU KOUZA, 14 (III), pp 1332–1399.

Examples of formula (II) compounds include ethylenediamine, N-(2-chloro-5-pyridylmethyl)ethylenediamine, N-(2-chloro-5thiazoylmethyl)ethylenediamine, and N-(2-chloro-5-pyridylmethyl)-N'-methylethylenediamine.

Preparation of the novel compound of this invention, i.e., formula (I) starting material, is illustrated as follows:

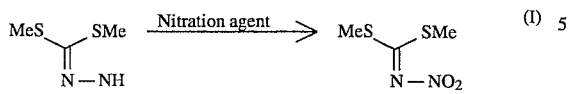

For an example of the nitrating agent shown in the reaction formula described above, the combination of a nitric acid or a nitric acid salt and an acid anhydride can be exemplified.

For examples of nitric acid salts, ammonium nitrate, sodium nitrate and copper nitrate can be exemplified, and the amount of nitric acid and the salts used is in a range of from 1 to 10 equivalents relatively to 1 equivalent of the above starting compound formula (I), preferably 1 to 4 equivalents from the economical point of view.

For examples of acid anhydrides, anhydrides of organic acids such as acetic anhydride and trifluoracetic anhydride, and anhydrides of inorganic acids such as phosphorous pentaoxide can be exemplified. The amount of the acid anhydride to be used is in a range of from 1 to 20 equivalents relatively to 1 equivalent of the above starting compound. However, in a case of liquid acid anhydrides such as acetic anhydride and trifluoroacetic anhydride, they sometimes function as a solvent when excess quantities thereof were used.

Although the reaction described above does not always require a solvent, solvents inactive to reactive reagents, for example, acids such as acetic acid and halogen-containing solvent such as chloroform, can be used for the reaction as well.

The temperature applicable for the above reaction is in a range of from $-50°$ C. to $100°$ C., and preferably from $-20°$ C. to $30°$ C. In addition, the reaction tends to be promoted by addition of chloride ions derived from a catalytic amount of sulfuric acid or hydrochloric acid to the reactant at conducting the reaction.

Based on one mole of the ester of N-nitroimidodithiocarbonic acid represented by formula (I), 1.0 to 3.0 mole, preferably 1.0 to 1.5 mole, of the diamines of formula (II) may be used.

The reaction solvent may not be particularly limited so long as it is inert to the reagents and the reaction. Generally, a halogenated hydrocarbon such as chloroform or dichloromethane, an alcohol such as methanol or ethanol, and an aromatic hydrocarbon such as toluene or chlorobenzene, and the like, may be used.

The reaction temperature may be from $-30°$ C. to the boiling point of the selected solvent. Generally, the reaction can proceed at room temperature.

After completion of the reaction, the desired product with high purity can be obtained by a direct filtration of deposited crystals from the reaction mixture. It can also be obtained by common post-treatment such as recrystallization or column chromatography of residue material after evaporation of the solvent.

When either $R^3$ or $R^4$ is hydrogen or both $R^3$ and $R^4$ are hydrogen, tautomeric isomers of the desired formula (III) product may exist as follows:

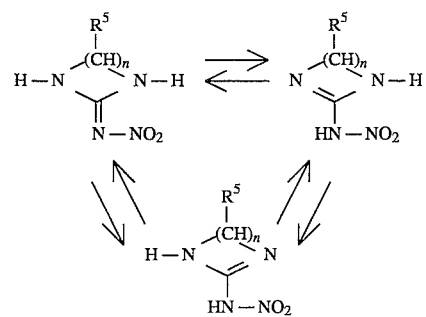

The present invention is described in more detail in the following examples. However, it should be noted that the invention shall not be limited to the examples shown.

EXAMPLE 1

N-nitroimidodithiocarbonate dimethyl ester

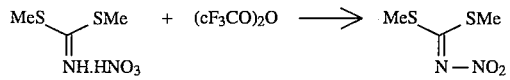

1.84 g (10 mmol) of imidodithiocarbonate dimethyl ester nitrate was suspended in 10 ml of chloroform, then 4.20 g (20 mmol) of trifluoracetic anhydride was fed dropwise thereto for 38 min. at a temperature range of from $-5°$ C. to $-10°$ C. with stirring. After stirring for 6.5 hours at a temperature range of from $-10°$ C. to $-15°$ C., the reacting solution was poured into 50 ml of ice water.

An extraction was made with 30 ml of chloroform, and the chloroform layer was dried with magnesium sulfate, then the solvent was removed by distillation under reduced pressure. The residue obtained was purified by using silica gel column chromatography (Solvent for elution; ethyl acetate:n-hexane=1:9), to give 0.68 g of the objective product. The yield was 41%.

EXAMPLE 2

N-nitroimidodithiocarbonate S-isopropyl S-methyl ester

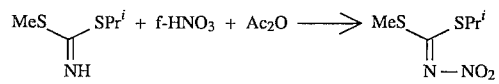

In 122.4 g (1.2 mol) of acetic anhydride was fed dropwise 25.2 g (0.4 mol) of fuming nitric acid for 8 min. with stirring at $15°$ C. or below. After stirring for 30 min. at a temperature range of from $10°$ C. to $15°$ C., 0.3 g of concentrated sulfuric acid was added to the solution at $0°$ C., then 29.8 g (0.2 mol) of imidodithiocarbonate S-isopropyl S-methyl ester was further added dropwise thereto for 30 min. at a temperature range of from $-2°$ C. to $2°$ C.

After dropping, the reacting solution was stirred for 40 min. at $0°$ C., then poured into 500 ml of ice water and followed by an extraction with methylene chloride. The methylene chloride layer was then dried with magnesium sulfate and the solvent was removed by distillation under reduced pressure. The residue obtained was purified by using silica gel column chromatography (Solvent for elution; ethyl acetate:n-hexane=1:10), to give 26.4 g of the objective oily product. The yield was 68.1%. $n_D^{25}$ was 1.5728.

NMR spectrum(CDCl$_3$) ppm: 1.43 ((Me)$_2$—CH—, d, 6H), 2.56 (S—CH$_3$, s, 3H), 3.82 and 4.02 (CH—, broad s, 1H) MASS spectrum(CI-GC): 195, 148 IR spectrum (KBr Plate, neat)cm$^{-1}$: 2900, 1540, 1260

EXAMPLE 3

N-nitroimidodithiocarbonate S-t-butyl S-methyl ester

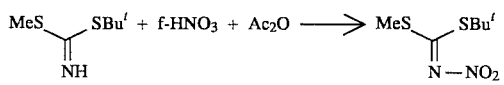

In 21.03 g (206 mmol) of acetic anhydride was fed dropwise 4.32 g (69 mmol) of fuming nitric acid with stirring at 10° C. After stirring for 30 min. at 15° C., 2 drops of concentrated sulfuric acid was added to the solution at 0° C., then 5.60 g (34 mmol) of imidodithiocarbonate S-t-butyl S-methyl ester was further added dropwise thereto for 27 min. at a temperature range of from −2° C. to 3° C.

After stirring for 45 min. at a temperature range of from 0° C. to −2° C., the reacting solution was poured into ice water and further extracted with methylene chloride. The methylene chloride layer was then dried with magnesium sulfate and the solvent was removed by distillation under reduced pressure. The residue obtained was purified by using silica gel column chromatography (Solvent for elution; ethyl acetate:n-hexane=1:30), to give 2.62 g of the objective oily product. The yield was 37.0%. $n_D^{25}$ was 1.5647.

NMR spectrum(CDCl$_3$) ppm: 1.61 ($^t$Bu, s, 9H), 2.55 (SMe, s, 3H) MASS spectrum(CI-CG): 209, 153

REFERENCE EXAMPLE

Dimethyl N-nitroimidodithiocarbonate:

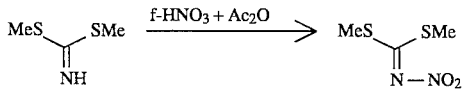

Into 122.4 g (1.2 mol) of acetic acid anhydride, 25.2 g (0.4 mol) of fuming nitric acid (sp. gr. 1.52) was dropped with stirring over 10 minutes while maintaining a temperature below 10° C. After cooling to 0° C., 0.3 g of conc. sulfuric acid and 24.2 g (0.2 mol) of dimethyl imidodithiocarbonate was dropped over 30 minutes into the mixture while maintaining a temperature of −5° C. to 5° C. The reaction mixture was stirred at −5° C. to 0° C. for 70 minutes; then, the reaction mixture was poured into 1 liter of ice water and the whole reaction mixture and water was stirred for 30 minutes.

The deposited crystals were filtered, washed with water and 20.6 g of the desirable compound was obtained by drying. The yield was 62.0%. Melting point 65° C.–65.5° C. and, $^1$H-NMR spectrum (CDCl3) ppm: 2.62 (SCH3,s) MASS spectrum (C1-D1): 167, 120, 74

EXAMPLE 4

2-(Nitroimino)imadazolidine:

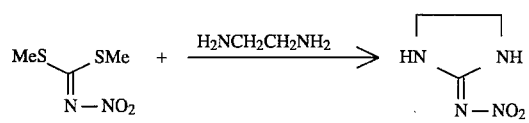

To a solution of 1.66 g (10 mmol) of dimethyl N-nitroimidodithiocarbonate in 5 ml of chloroform, a solution of 0.72 g (12 mmol) of ethylenediamine in 1 ml of chloroform was added with stirring at 27° C. to 33° C. under cooling by ice water.

The reaction mixture was stirred at room temperature for 3 hours followed by evaporation of the solvent under reduced pressure. The deposited crude crystal was collected and washed by diethyl ether. 1.25 g of the desired crystalline compound was obtained by drying. The yield was 96.1%. Melting point 213° C.–215° C. (decomposed).

EXAMPLE 5

2-(Nitroimino)imadazolidine:

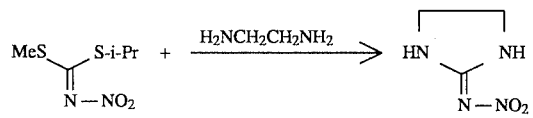

To a solution of 1.94 g (10 mmol) of S-isopropyl S'-methyl N-nitroimidodithiocarbonate in 5 ml of chloroform, a solution of 0.66 g (1 mmol) of ethylenediamine in 1 ml of chloroform was added with stirring at 25° C. to 30° C. under cooling by ice water.

The reaction mixture was stirred at room temperature for 1.5 hours followed by the same treatment as Example 1. Thus, 1.20 g of the desired crystalline compound was obtained. The yield was 92.3%.

EXAMPLE 6

1-Methyl 2-(nitroimino)imidazolidine:

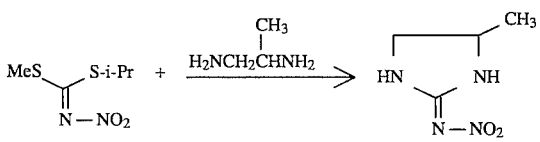

To a solution of 1.66 g (10 mmol) of dimethyl N-nitroimidodithiocarbonate in 5 ml of chloroform, a solution of 0.81 g (11 mmol) of 1,2-propanediamine in 1 ml of chloroform was added with stirring at 28° C. to 38° C. under cooling by ice water.

The reaction mixture was stirred at room temperature for one hour followed by the same treatment as Example 1. Thus, 1.29 g of the desired crystalline compound was obtained. The yield was 89.6%. Melting point 172° C.–3° C.

EXAMPLE 7

1-Methyl 2-(nitroimino)imidazolidine:

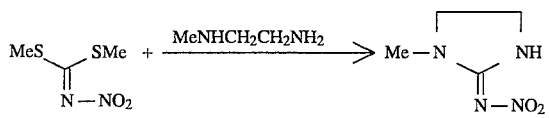

To a solvent solution of 1.66 g (10 mmol) of dimethyl N-nitroimidodithiocarbonate, 0.82 g (11 mmol) of N-methylethylenediamine was added with stirring at 20° C. to 28° C. under cooling by ice water.

The reaction mixture was stirred at room temperature for 3 hours followed by evaporating the solvent under reduced pressure. The crude crystal was recrystallized from ethanol and dried. Thus, 1.17 g of the desired compound was obtained. The yield was 81.3%. Melting point 115° C.–116.5° C.

EXAMPLE 8

1-(2-Chloro-5-pyridylmethyl)-2-(nitroimino)imidazolidine:

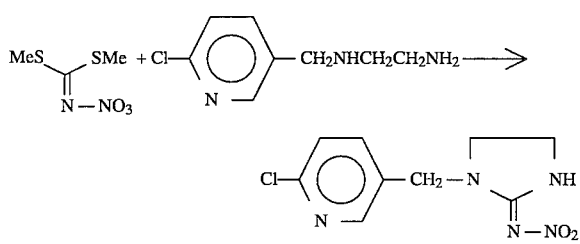

To a solution of 2.50 g (15 mmol) of dimethyl N-nitroimidodithiocarbonate in 10 ml of dichloromethane, 2.78 g (15 mmol) of N-(2-chloro-5-pyridylmethyl)ethylenediamine was added with stirring at 25° C. to 32° C. under ice cooling.

The reaction mixture was stirred at room temperature for 3 hours, followed by evaporating the solvent under reduced pressure. The crude crystal deposited was recrystallized from ethanol and dried. Thus, 3.07 g of the desired compound was obtained. The yield was 80.0%. Melting point 134° C.–6° C.

EXAMPLE 9

2-(Nitroimino)1,3-diazacyclohexane:

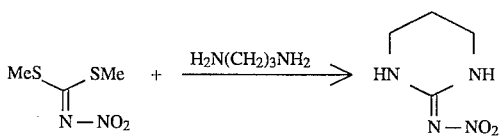

To a solution of 1.66 g (10 mmol) of dimethyl N-nitroimidodithiocarbonate in 5 ml of chloroform, 0.82 g (11 mmol) of trimethylenediamine was added with stirring at 25° C. to 37° C. under ice cooling.

After the reaction mixture was stirred at room temperature for one hour, the crude crystal deposited was filtered, washed with chloroform and dried. Thus, 1.14 g of the desired compound was obtained. The yield was 79.2%. Melting point 246° C.–248° C. (decomposed).

EXAMPLE 10

2-(Nitroimino)1,3-diazacycloheptane:

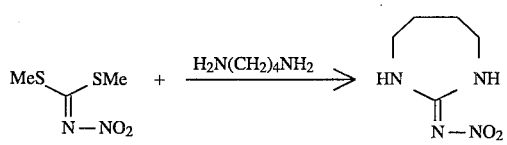

To a solution of 1.66 g (10 mmol) of dimethyl N-nitroimidodithiocarbonate in 5 ml of chloroform, 0.97 g (11 mmol) of tetramethylenediamine was added with stirring at 25° C. to 32° C. under ice cooling.

The reaction mixture was stirred at room temperature for 1.5 hours, and treated as Example 6. Thus, 1.42 g of the desired compound was obtained. The yield was 89.9%. Melting point 182° C.–4° C.

COMPARATIVE EXAMPLE 1

2-(Nitroimino)imadazolidine:

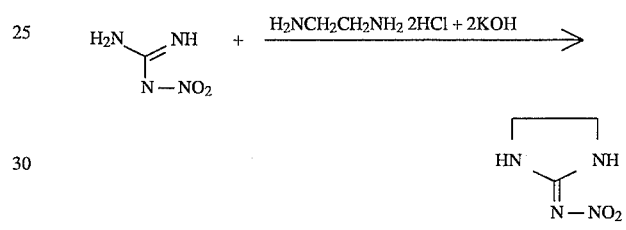

To a 50 ml of aqueous solution of 22.4 g of potassium hydroxide (0.4 mol), 20.8 g (0.2 mol) of nitroguanidine, 26.6 g (0.2 mol) of ethylenediamine di-hydrochloride were subsequently added with stirring at room temperature. The reaction mixture was heated to 65° C. to 70° C. for 20 minutes and then cooled to 1° C. The deposited crystal was filtered and washed with small portion of cold water and dried. Thus, 9.6 g of the desired crystalline was obtained. The yield was 37%.

Comparing the Example 4 and 5 based on the preparation method in the present invention with Comparative Example 1, it is remarkable that yields of the desired nitrogen containing heterocycles are significantly improved by the method of the present invention.

A compound, for example, given in Example 8, among the compounds prepared according to the invention, is useful as a insecticide.

What is claimed:

1. A compound of the formula

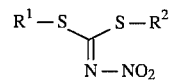

wherein $R^1$ and $R^2$ are the same or different from each other and denote lower alkyl of 1 to 4 carbon atoms.

2. N-nitroimidodithiocarbonate s-t-butyl s-methyl ester.

3. N-nitroimidodithiocarbonate s-isopropyl s-methyl ester.

4. N-nitroimidodithiocarbonate dimethyl ester.

* * * * *